(12) United States Patent
Besson

(10) Patent No.: US 8,781,062 B2
(45) Date of Patent: Jul. 15, 2014

(54) DYNAMIC ADJUSTMENT OF X-RAY ACQUISITION PARAMETERS

(75) Inventor: Guy M. Besson, Danvers, MA (US)

(73) Assignee: Analogic Corporation, Peabody, MA (US)

( * ) Notice: Subject to any disclaimer, the term of this patent is extended or adjusted under 35 U.S.C. 154(b) by 0 days.

(21) Appl. No.: 13/533,080

(22) Filed: Jun. 26, 2012

(65) Prior Publication Data

US 2013/0343515 A1     Dec. 26, 2013

(51) Int. Cl.
*G01N 23/04*     (2006.01)

(52) U.S. Cl.
USPC ..................... 378/16; 378/4; 378/19

(58) Field of Classification Search
CPC .............................. A61B 6/032; A61B 6/5235
USPC ............................................................ 378/16
See application file for complete search history.

(56) References Cited

U.S. PATENT DOCUMENTS

| | | | |
|---|---|---|---|
| 2005/0075563 A1* | 4/2005 | Sukovic et al. ............... | 600/427 |
| 2008/0187095 A1* | 8/2008 | Boone et al. ..................... | 378/37 |
| 2009/0252285 A1* | 10/2009 | Shapiro et al. .................... | 378/8 |
| 2011/0058645 A1* | 3/2011 | Heuscher ......................... | 378/16 |
| 2011/0150175 A1* | 6/2011 | Hsieh et al. ..................... | 378/16 |

* cited by examiner

*Primary Examiner* — Hoon Song
*Assistant Examiner* — Danielle Fox
(74) *Attorney, Agent, or Firm* — Cooper Legal Group LLC

(57) ABSTRACT

Among other things, one or more techniques and/or systems are described for dynamically adjusting one or more X-ray acquisition parameters of an X-ray imaging modality. During a first portion of an examination of an object, the object is examined using a first set of X-ray acquisition parameters and a first image is generated. A region-of-interest is identified in the first image and one or more X-ray acquisition parameters are adjusted as a function of the identified region-of-interest to establish a second set of X-ray acquisition parameters. During a second portion of the examination of the object, the object is examined using the second set of X-ray acquisition parameters to generate a second image. In this way, X-ray acquisition parameters can be adjusted in real-time or 'on the fly' to obtain a (more) desired image.

20 Claims, 5 Drawing Sheets

DYNAMIC ADJUSTMENT OF X-RAY ACQUISITION PARAMETERS

BACKGROUND

The present application relates to the field of X-ray imaging. It finds particular relevance to projection and computed tomography (CT) imaging systems such as utilized in medical, security, industrial and/or other applications. It also relates to other forms of X-ray imaging systems where dynamically adjusting X-ray acquisition parameters may be useful.

Today, CT and other X-ray imaging modalities (e.g., mammography systems, projection radiography systems, scanning line systems, etc.) are useful to provide information, or images, of interior aspects of an object under examination. Generally, the object is exposed to X-ray radiation comprising X-ray photons, and an image(s) is formed based upon the radiation absorbed and/or attenuated by interior aspects of the object, or rather an amount of photons that is able to pass through the object. Generally, highly dense aspects of the object absorb and/or attenuate more radiation than less dense aspects, and thus an aspect having a higher density, such as a bone or metal, for example, may be apparent when surrounded by less dense aspects, such as muscle or clothing.

To construct an image, X-ray radiation is emitted and information is acquired according to X-ray acquisition parameters that specify, among other things, an X-ray tube current and/or voltage, beam filtration, data filtration, etc., for example. The information acquired from the X-ray examination is then reconstructed or assembled to form an image which a user, such as a radiologist or security personnel, can view.

Presently, X-ray tube current may be dynamically adjusted during an examination as a function of the view angle in CT (e.g., which may be known to those skilled in the art as an 'auto mA' functionality) and/or as a function of an auto-exposure feature in a projection acquisition. However, other X-ray acquisition parameters are not known to be adjusted during the examination. This is in contrast to ultrasound imaging, where imaging parameters may be dynamically adjusted by a clinician during the examination as a function of the visual representation of the object to improve the representation of a desired aspect of the object. For example, during an ultrasound examination, a clinician may alter the frequency of the ultrasound waves and/or make other adjustments that improve the image quality or usefulness of the image with respect to an aspect of the object that is of particular interest.

SUMMARY

Aspects of the present application address the above matters, and others. According to one aspect, a method for dynamically adjusting X-ray acquisition parameters in an X-ray imaging modality is provided. The method comprises examining an object using a first set of X-ray acquisition parameters and generating a first image representative of the object based upon the examination using the first set of X-ray acquisition parameters. The method also comprises identifying a region-of-interest in the first image and adjusting one or more X-ray acquisition parameters of the first set of X-ray acquisition parameters based upon the identified region-of-interest to yield a second set of X-ray acquisition parameters. The method further comprises reexamining the object using the second set of X-ray acquisition parameters.

According to another aspect, a system for dynamically adjusting X-ray acquisition parameters in an X-ray imaging modality is provided. The system comprises an X-ray parameters component configured to dynamically adjust X-ray acquisition parameters in an X-ray imaging modality between a first portion of an examination of an object and a second portion of the examination. The first portion of the examination yields a first image from which a region-of-interest is identified, and the X-ray parameters component is configured to dynamically adjust one or more X-ray acquisition parameters based upon the identified region-of-interest.

According to yet another aspect, a computer readable medium comprising computer executable instructions that when executed via a processing unit perform a method is provided. The method comprises examining an object using a first set of X-ray acquisition parameters and generating a first image representative of the object based upon the examination using the first set of X-ray acquisition parameters. The method also comprises identifying a region-of-interest in the first image and adjusting one or more X-ray acquisition parameters of the first set of X-ray acquisition parameters based upon the identified region-of-interest to yield a second set of X-ray acquisition parameters. The method further comprises reexamining the object using the second set of X-ray acquisition parameters.

FIGURES

The application is illustrated by way of example and not limitation in the figures of the accompanying drawings, in which like references indicate similar elements and in which.

DESCRIPTION

Figure 1:
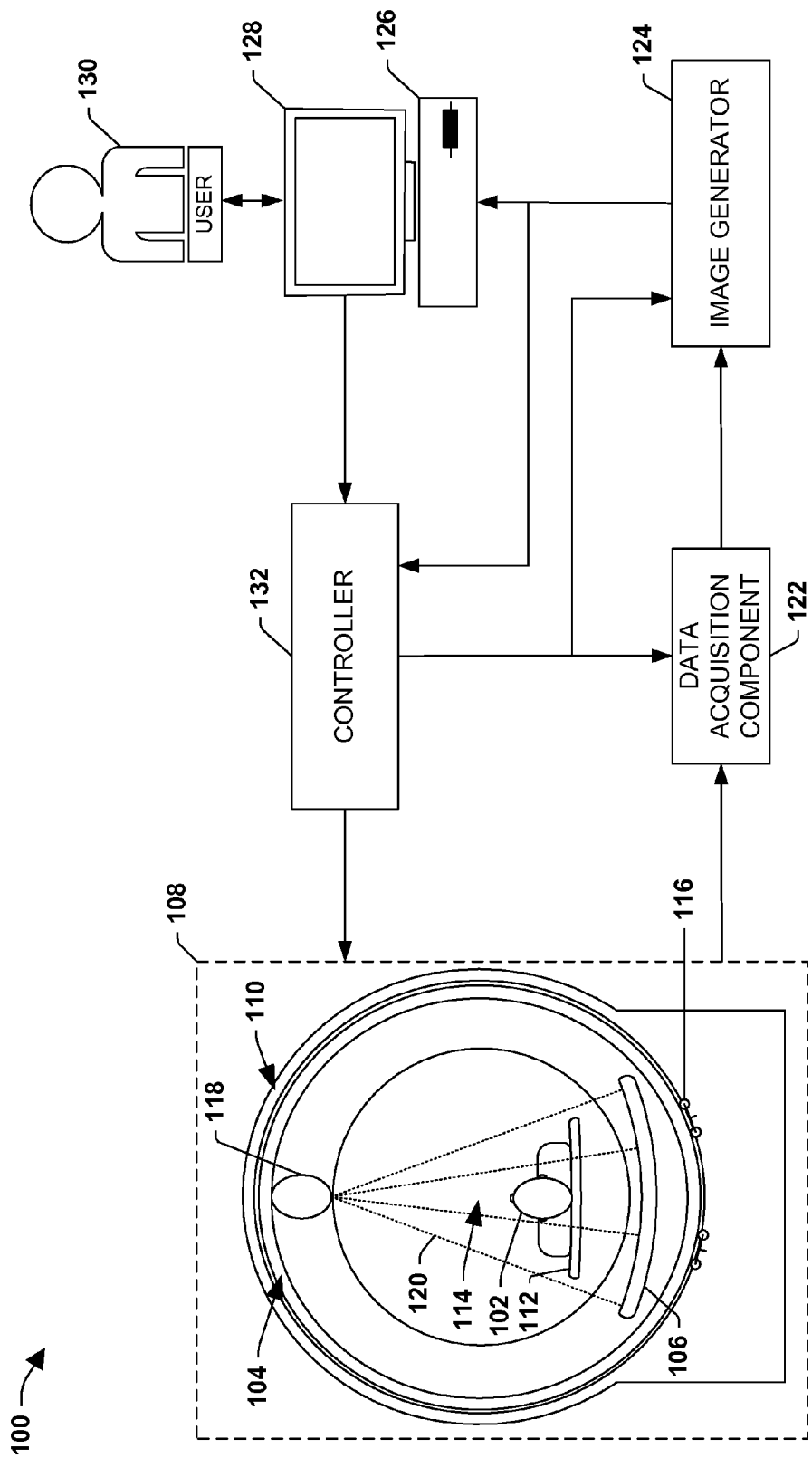
FIG. 1 is a schematic block diagram illustrating an example examination environment for examining an object.

The claimed subject matter is now described with reference to the drawings, wherein like reference numerals are generally used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are illustrated in block diagram form in order to facilitate describing the claimed subject matter.

One or more techniques and/or systems for dynamically adjusting one or more X-ray acquisition parameters during an examination of an object are provided for herein. Typically, the object is initially exposed to a low-dose of radiation (e.g., a dose of radiation insufficient to produce an image of diagnostic quality) and a region-of-interest is identified in a resulting low-dose image. Based upon the identified region-of-interest, one or more X-ray acquisition parameters are adjusted (relative to the settings of the X-ray acquisition parameters at the time of the initial, low-dose exposure) to improve data acquisition with respect to the region-of-interest, and the object is re-exposed, at higher dose of radiation (e.g., a dose of radiation sufficient to produce an image of diagnostic quality). That is, stated differently, one or more X-ray acquisition parameters are set as a function of the identified region-of-interest to improve the usefulness of resulting images, such as with respect to the region-of-interest (e.g., with the parameters being set to improve the diagnostic usefulness of the image with respect to the region-of-interest), and the object is exposed to a higher dose of radiation to generate another image (e.g., a diagnostic image). It may be appreciated that adjusting the X-ray acquisition parameters as a function of the identified region-of-interest may include adjusting the dosage or the dosage may be increased without consideration of the region-of-interest. For example, in one embodiment, a spatial resolution of a detector array may be altered as a function of the identified region-of-interest and the dosage may be adjusted to a predefined level (e.g., that is not a function of the identified region) to increase image quality (e.g., to reduce image artifacts) relative to the image yielded from the lower-dose exposure. That is, the dosage is generally increased to obtain a diagnostic quality image, and the increase in dosage may or may not be a function of the identified region-of-interest (e.g., may automatically be increased to a predefined level or may be increased to a particular level based upon the identified region-of-interest).

As will be described further, the region-of-interest may be identified automatically or manually, and the one or more X-ray acquisition parameters that are adjusted/set as a function of the identified region-of-interest may be adjusted/set automatically or manually. For example, in one embodiment, a user may specify an organ of interest (e.g., such as a heart) and the system may automatically scan one or more low-dose images to identify a region of the image comprising the heart. In another embodiment, the low-dose image(s) may be displayed on a monitor, for example, and the user may highlight or select a region-of-interest within the image(s), for example. Further, a menu comprising one or more options for adjusting the X-ray acquisition parameters may be displayed, and the user may select options in the menu for altering/setting the X-ray acquisition parameters. Alternatively, the system may be configured to automatically determine how to adjust one or more of the X-ray acquisition parameters based upon the selection of the region-of-interest and/or based upon the contents of the region-of-interest (e.g., based upon what is represented in the region-of-interest). For example, the system may analyze the identified region-of-interest to identify contents represented in the region-of-interest and may adjust/set one or more X-ray acquisition parameters according to the identified contents. By way of example, X-ray acquisition parameters that are set when the region-of-interest represents a lung may be different than the X-ray acquisition parameters set when the region-of-interest represents a heart. Further, these pre-defined settings, once automatically selected, may be further adjusted by a user. Furthermore, in the case of a CT modality, analysis of a region-of-interest may comprise analysis of substantially all the projection data utilized to reconstruct an image of the region-of-interest; including a total attenuation path for X-ray lines passing through the region-of-interest, which may comprise information pertaining to the attenuation of objects located outside the region-of-interest.

Moreover, in one embodiment, image data acquired from the low-dose, initial examination may be combined with historical image data of the object to reduce artifacts in an image resulting from the low-dose examination, for example. By way of example, image data from an examination performed several years ago may be combined with image data produced from the low-dose examination (e.g., which provides information regarding the present orientation of the object relative to an support article supporting the object) to reduce artifacts in an image produced from the low-dose examination. Further, by co-registering and/or combining historical image data with the image data from the low-dose examination, the object may be exposed to an even lower dose of low-dose X-ray radiation relative to the low-dose applied if the image data from the low-dose examination is not combined with historical image data.

It may be appreciated that the techniques and/or systems described herein may find applicability to both single-energy and multi-energy (e.g., dual-energy) X-ray imaging modalities. Moreover, such techniques and/or systems may apply to, among other things, integration-type imaging modalities (e.g., where charge is integrated over time) and photon counting-type imaging modalities (e.g., where the number of photons detected are individually counted and recorded), for example. It may also be appreciated that the foregoing features are merely example features intended to describe one embodiment of the systems/techniques described herein. Other features and/or embodiments may be realized in view of the following disclosure.

FIG. 1 is an illustration of an example environment 100 comprising a computed tomography (CT) system that may be configured to generate images representative of an object 102 (e.g., baggage, patient, etc.) or aspect(s) thereof under examination and to dynamically adjust one or more X-ray acquisition parameters as a function of an identified region-of-interest in an image produced during the examination.

It may be appreciated that while the example environment 100 describes a CT system configured to generate two-dimensional, three-dimensional, four-dimensional, etc. images of the object 102 under examination, other X-ray imaging modalities are also contemplated. For example, scanning line systems and/or projection systems may be utilized to generate two-dimensional images of an object. Moreover, the arrangement of components and/or the types of components included in the example environment 100 are merely provided as examples. By way of example, in another embodiment, the data acquisition component 122 may be comprised within the detector array 106.

In the example environment 100, an examination unit 108 of the CT system is configured to examine one or more objects 102. The examination unit 108 can comprise a rotating gantry 104 and a (stationary) support structure 110 (e.g., which may encase and/or surround at least a portion of the rotating gantry 104 (e.g., as illustrated with an outer, stationary ring, surrounding an outside edge of an inner, rotating ring)). During an examination of the object(s) 102, the object (s) 102 can be placed on a support article 112, such as a bed or conveyor belt, for example, that is selectively positioned in an examination region 114 (e.g., a hollow bore in the rotating gantry 104), and the rotating gantry 104 can be rotated and/or supported about the object(s) 102 by a rotator 116, such as a motor, drive shaft, chain, roller truck, etc.

The rotating gantry 104 may surround a portion of the examination region 114 and may comprise one or more X-ray sources 118 and a detector array 106 that is mounted on a substantially diametrically opposite side of the rotating gantry 104 relative to the X-ray source(s) 118.

During an examination of the object(s) 102, the X-ray source(s) 118 emits fan, cone, wedge, and/or other shaped X-ray 120 configurations from a focal spot(s) of the X-ray source(s) 118 (e.g., a region within the X-ray source(s) 118 from which X-rays 120 emanate) into the examination region 114. It may be appreciated that such X-rays 120 may be emitted substantially continuously and/or may be emitted intermittently (e.g., a brief pulse of X-rays is emitted followed by a resting period during which the X-ray source 118 is not activated).

As the emitted X-rays 120 traverse the object(s) 102, the X-rays 120 may be attenuated differently by different aspects of the object(s) 102. Because different aspects attenuate different percentages of the X-rays 120, an image(s) may be generated based upon the attenuation, or variations in the number of photons that are detected by the detector array 106. For example, more dense aspects of the object(s) 102, such as a bone or metal plate, may attenuate more of the X-rays 120 (e.g., causing fewer photons to strike the detector array 106) than less dense aspects, such as skin or clothing.

The detector array 106 is configured to directly convert (e.g., using amorphous selenium and/or other direct conversion materials) and/or indirectly convert (e.g., using scintillators and/or other indirect conversion materials) detected radiation into signals that can be transmitted from the detector array 106 to a data acquisition component 122 configured to compile signals that were transmitted within a predetermined time interval, or measurement interval, using various techniques (e.g., integration, photon counting, etc.). It may be appreciated that such a measurement interval may be referred to as a "view" and generally reflects signals generated from X-rays 120 that were emitted while the radiation source 118 was at a particular angular range relative to the object 102. Based upon the compiled signals, the data acquisition component 122 can generate projection data indicative of the compiled signals, for example, and the compilation of projection data from a plurality of views may allow volumetric data to be generated from the examination.

The example environment 100 further comprises an image generator 124 configured to receive the projection data that is output by the data acquisition component 122. The image generator 124 is configured to generate image data (also referred to as image(s)) from the projection data using a suitable analytical, iterative, and/or other reconstruction technique (e.g., backprojection reconstruction, tomosynthesis reconstruction, iterative reconstruction, etc.). In this way, the data is converted from projection space to image space, a domain that may be more understandable by a user 130 viewing the image(s), for example.

The example environment 100 further comprises a terminal 126, or workstation (e.g., a computer), that may be configured to receive the image data (e.g., output by the image generator 124). The terminal 126 may also be configured to present the image data for display on a monitor 128 to a user 130 (e.g., security personnel, medical personnel, etc.). In this way, the user 130 can inspect the image(s) to identify areas of interest within the object(s) 102 and/or to identify a region-of-interest in an image. The terminal 126 can also be configured to receive user input which can direct operations of the object examination apparatus 108 (e.g., a speed to rotate, a speed and direction of a conveyor belt, etc.) and/or which can direct adjustments to one or more X-ray acquisition parameters during the continued examination of the object 102, for example.

In the example environment 100, a controller 132 is operably coupled to the terminal 126. The controller 132 may be configured to control operations of the examination unit 108, the data acquisition component 122, and/or the image generator 124. By way of example, in one embodiment, the controller 132 may be configured to receive information from the terminal 126 indicative of a request to alter one or more X-ray acquisition parameters during an examination of the object 102, and the controller 132 may be configured to issue instructions to the examination unit 108, the data acquisition component 122, and/or the image generator 124 indicative of the request. In another embodiment, the controller 132 may be configured to scan/examine an initial image of the object 102 (e.g., generated by the image generator 124) to identify a region-of-interest within the image and to issue instructions for changing one or more X-ray acquisition parameters based upon the identified region-of-interest. For example, the controller 132 may be configured to automatically identify a region-of-interest that corresponds to a user desired aspect of the object 102 (e.g., the heart, lungs, or other anatomical feature) and may, based upon the identified region-of-interest, automatically adjust one or more X-ray acquisition parameters to improve the representation of the aspect in the region-of-interest in subsequent images of the object 102, for example. Other control capabilities of the controller 132 may include, but are not limited to, providing instructions for maneuvering the support article 112 and/or turning on/off the examination unit 108, for example.

It may be appreciated that the example component diagram is merely intended to illustrate one embodiment of one type of imaging modality and is not intended to be interpreted in a limiting manner. For example, the functions of one or more components described herein may be separated into a plurality of components and/or the functions of two or more components described herein may be consolidated into merely a single component. Moreover, the imaging modality may comprise additional components configured to perform additional features, functions, etc. and/or some components described herein may be optional.

Figure 2:
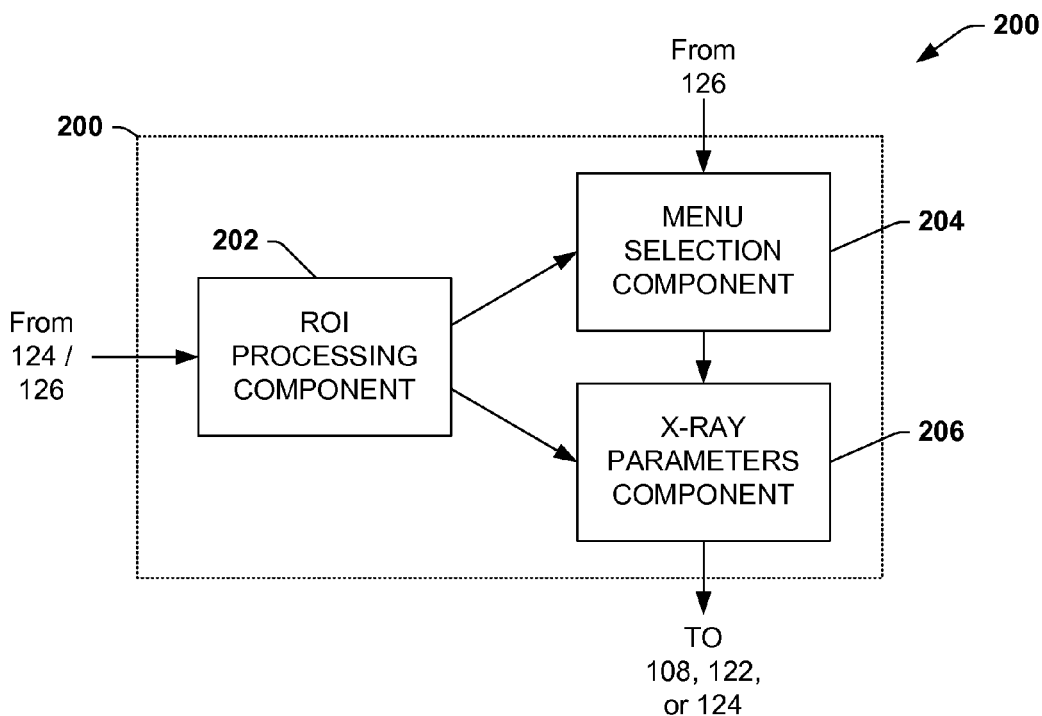
FIG. 2 illustrates a component block diagram of an example controller.

FIG. 2 illustrates a component block diagram of an example controller 200 (e.g., 132 in FIG. 1) configured to, among other things, dynamically adjust X-ray acquisition parameters in an X-ray imaging modality during an examination of an object based upon an identified region-of-interest in an image produced at least in part from information/data acquired during a first portion of the examination. That is, stated differently, the controller 200 is configured to dynamically adjust one or more X-ray acquisition parameters during an examination of the object such that a first portion of the examination is performed using a first set of X-ray acquisition parameters and a second portion of the examination is performed using a second set of X-ray acquisitions parameters that differ to some extent from the first set of X-ray acquisition parameters. X-ray acquisition parameters that the controller 200 is configured to dynamically adjust may include, but are not limited to, X-ray tube current, X-ray tube voltage, X-ray beam shape (e.g., spatial extent (in all directions) via collimation, 'bow-tie' pre-patient spatial filtering of the X-ray beam, etc.), X-beam filtration, detector spatial resolution, temporal resolution, digital acquisition system filter parameters (e.g., configured to filter frequencies of signals at the data acquisition component 122 in FIG. 1), and/or image reconstruction/generation filter parameters (e.g., configured to filter frequencies of signals at the image generator 124 in FIG. 1). It may be appreciated that by dynamically adjusting one or more X-ray acquisition parameters as a function of a region-of-interest identified in an image produced at least in part from a first portion of the examination, data/information acquired during a second portion of the examination may be more tailored to the region-of-interest to improve image quality with respect to the region-of-interest and/or to provide additional/different information about the aspect(s) of the object represented in the region-of-interest relative to the information provided in an image(s) produced during the first portion of the examination.

The example controller 200 may comprise, among other things, a region-of-interest (ROI) processing component 202, a menu selection component 204, and/or an X-ray parameters component 206 for dynamically adjusting X-ray acquisition parameters. It may be appreciated that the controller 200 may comprise additional and/or different components depending upon, among other things, the functions of the controller 200. For example, if the controller 200 is configured to control movement of a support article (112 in FIG. 1), the controller 200 may also comprise a component for controlling such movement. Moreover, it may be appreciated that although the ROI processing component 202, the menu selection component 204, and the X-ray parameters component 206 are illustrated as comprised within a controller 200, one or more components may be located outside of the controller 200. Further, the functions of one or more components described herein may be separated into a plurality of components and/or the functions of two or more components described herein may be consolidated into merely a single component.

The ROI processing component 202 is configured to identify or define a region-of-interest in an image representative of data acquired during the first portion of the examination (e.g., generated by an image generator 124 in FIG. 1). Such an identification/definition may be the result of user input (e.g., where a user selects the region-of-interest and information is sent to the ROI processing component 202 from a terminal 126 in FIG. 1) and/or may be the result of an automatic identification process.

As an example, in one embodiment, a first image, representative, at least in part, of data acquired during a first portion of the examination, may be displayed to a user (e.g., on a display 128 in FIG. 1) along with a region-of-interest window. As further described with respect to FIG. 3, the user may navigate the region-of-interest window and/or alter the size of the region-of-interest window to define a region-of-interest within the first image. In such an embodiment, the ROI processing component 202 may be configured to receive information regarding the user input, process the information, and forward the processed information to an X-ray parameters component 206 (e.g., where the identified region-of-interest may be utilized to adjust one or more X-ray acquisition parameters).

As another example of a more automated identification process, the ROI processing component 202 may be configured to receive the first image (e.g., from the image generator 124 and/or from the terminal 126) and may be configured to examine/scan the first image to identify a region-of-interest. By way of example, the ROI processing component 202 may utilize analytical, iterative, and/or other object identification techniques (e.g., such as threat-detection techniques) to analyze/examine the first image and to identify potential areas of interest based upon the application (e.g., security, cancer detection, heart imaging, etc.) of the X-ray imaging modality. Areas that the ROI processing component 202 identifies as potential areas of interest may be labeled as regions-of-interest and information regarding such regions-of-interest (e.g., which may include attenuation information from objects located outside the ROI that contribute to the projection data utilized to reconstruct the ROI) may be transmitted to the X-ray parameters component 206 from the ROI processing component 202, for example.

The example controller 200 may further comprise a menu selection component 204 configured to receive a selection of a menu option regarding one or more desired adjustments to the X-ray acquisition parameters. By way of example, as further described in FIG. 4, upon the identification of a region-of-interest (e.g., by a user and/or by the ROI processing component 502), a presentation component, for example, may be configured to provide for presentation (e.g., on the display 128 of FIG. 1) a menu comprising options for dynamically adjusting one or more X-ray acquisition parameters. If the user, for example, makes a selection of one or more menu options from the presented menu, an indication of such may be transmitted from a terminal (e.g., 126 in FIG. 1) to the menu selection component 204, for example, configured to receive an indication of such a selection, such as "lowest diagnostic dose," "optimal contrast (at a set dose level)," or "collimate the beam to region-of-interest (ROI)" for example. Moreover, the menu selection component 204 may be configured to provide the X-ray parameters component 206 with information regarding the received indication, which may further assist the X-ray parameters component 206 in determining how to adjust one or more X-ray acquisition parameters based upon the identified region-of-interest.

The X-ray parameters component 206 is configured to dynamically adjust one or more X-ray acquisition parameters in an X-ray imaging modality between a first portion of an examination of an object and a second portion of the examination of the object based upon the identified region-of-interest and/or a menu selection from a menu of options for adjusting X-ray acquisition parameters. That is, stated differently, the X-ray parameters component 206 is configured to receive information from the ROI processing component 202 related to the identification of a region-of-interest and (optionally) from the menu selection component 202 related to one or more desired adjustments to the X-ray acquisition parameter and is configured to utilize such information to dynamically adjust one or more X-ray acquisition parameters during an examination of an object (e.g., where a first portion of the examination may be defined as an interval of time when a first set of X-ray acquisition parameters are utilized to examine the object and a second portion of the examination may be defined as an interval of time when a second set of X-ray acquisition parameters are utilized to examine the object). It may be appreciated that X-ray acquisition parameters are typically parameters that affect how data is collected and/or filtered whereas image reconstruction parameters are typically parameters that affect how data is synthesized/combined to generate an image. It may also be appreciated that image reconstruction parameters may be fine-tuned and optimized based on a selection of x-ray acquisition parameters. For example, an image reconstruction filter (in filtered-back-projection CT image reconstruction approaches) may be adjusted and matched to a data-acquisition system filter as well as to a desired resolution in the region-of-interest, for example.

In one embodiment, at least one X-ray acquisition parameter may be adjusted automatically (e.g., without user input indicative of a desired change to the parameter). For example, in one embodiment, the X-ray parameters component 206 may be configured to identify a feature(s) comprised in the region-of-interest and to adjust one or more X-ray acquisition parameters automatically as a function of the contents of the object represented in the region-of-interest. For example, the X-ray parameters component 206 may be configured to utilize analytical, iterative, and/or other object recognition techniques to identify one or more objects comprised in the image and may adjust X-ray acquisition parameters according to the identified object(s). As such, in an embodiment where the X-ray parameters component 206 is configured to automatically adjust one or more X-ray acquisition parameters, the menu selection component 204 may be optional (e.g., and utilized to receive input that supplements or overrides the automatic adjustments of the X-ray parameters component 206).

Figure 3:
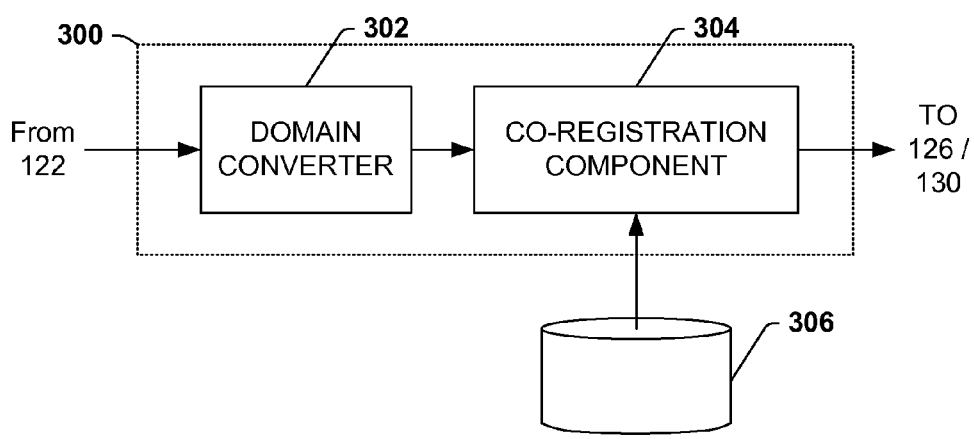
FIG. 3 illustrates a component block diagram of an example image generator.

The first image, indicative of data acquired during a first portion of the examination, is typically utilized to determine the orientation/position of the object under examination relative to the imaging system and/or a support article supporting the object and to identify a region-of-interest, for example. As such, the first image may not be considered a diagnostic-quality image, and the dose of radiation applied to the object during the first portion of the examination may be different than (e.g., less than) the dose of radiation applied to the object during a second portion of the examination from which a diagnostic-quality image may be produced, for example. It may be appreciated that the lower the dose of radiation, the more difficult it typically is to reconstruct an image void of substantial artifacts. As such, as illustrated in FIG. 3, an image generator 300 (e.g., 124 in FIG. 1) may be configured to combine image data acquired from the first portion of the examination (e.g., real-time information related to the orientation of the object and/or aspects comprised within the object) with historical image data representative of information about the object from a previously performed examination. For example, historical image data produced from an examination several years earlier may be co-registered and/or combined with image data produced during the (e.g., low-dose) first portion of the examination to generate a first image that is substantially free of artifacts. It may be appreciated that such an image may not necessarily be useful for diagnosing a patient/object, for example, because the image is generated at least in part from historical data (e.g., that may not be fully representative of the current state of a tumor). However, it may be useful for identifying a region-of-interest because a low-quality present-day examination (e.g., from which orientation information may be derived) is combined with (higher-quality) image data from a previous examination. Further, such historical data, when properly co-registered with the present-day acquisition data, may allow higher-dose, diagnostic level irradiation to be spatially limited in relation to a region-of-interest (ROI). That is, 'interior' reconstruction (also known as 'local' reconstruction) may be enabled by combining present-day data covering the ROI with historical data extending outside the ROI to produce an image substantially free of artifacts (e.g., which may not be able to be produced without historical data utilization, such as due to beam truncation). In such an embodiment, co-registration of the historical data with a first, low-dose part of the acquisition may allow the total examination dose to be substantially reduced, for example.

As illustrated, the component block diagram of the example image generator 300 comprises a domain converter 302 configured to convert data from a projection domain to an image domain using domain conversion techniques (e.g., backprojection, tomosynthesis reconstruction, interative reconstruction, etc.). More particularly, with respect to the first portion of the examination, the domain converter 302 may be configured to convert data acquired during the first portion of the examination into image data representative of the object under examination. Given that the first portion of the examination may expose the object to a dosage of radiation insufficient to produce a diagnostic image, the physics of X-ray imaging under limited irradiation may lead to artifacts in the image that reduce visibility in the image (e.g., such that some objects represented in the first image may appear smeared or otherwise difficult to discern).

In some embodiments (e.g., to improve the image quality of an image produced from information acquired during the first portion of the examination and/or to provide for exposing the object to an even lower dose of radiation during the first portion of the examination), the image generator 300 may comprise a co-registration component 304 configured to co-register the historical image data representative of the object with image data yielded from the first portion of the examination to generate the first image from which a region-of-interest may be identified, for example.

By way of example, the co-registration component 304 may be operably coupled to a storage device 306 and may be configured to retrieve and/or receive historical image data representative of the object under examination from the storage device 306. The co-registration component 304 may also be configured to co-register and/or combine the image data acquired from the first portion of the examination with the historical image data representative of the object, which may be acquired at a different time, on a different device, and/or with the object oriented in a different orientation relative to the imaging system and/or the support article, for example, to generate a first image that may be output by the co-registration component 304 to a terminal (e.g., 126 in FIG. 1) and/or a controller (e.g., 132 in FIG. 1), for example. In this way, the first image from which a region-of-interest is identified may comprise fewer artifacts than what may have been produced had the first image been generated merely from the first portion of the examination, for example. Further, by combining historical image data with image data yielded from the first portion of the examination, the first portion of the examination may expose the object to less radiation than may be required if the image data from the first portion of the examination is not combined with the historical image data, for example. Moreover, co-registration of historical data with data acquired during the first examination portion may enable reduced collimation of the beam during the second portion of the examination, thus leading to significant overall reduction in delivered x-ray dose, for example.

Figure 4:
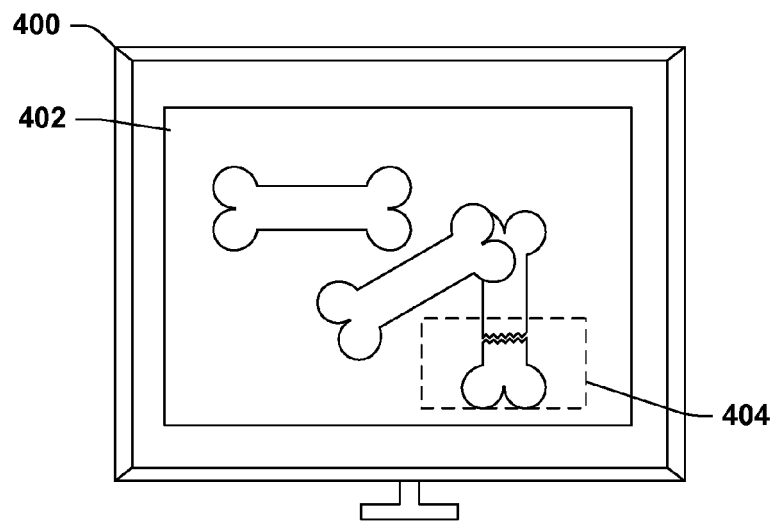
FIG. 4 illustrates an example user interface displaying a first image of an object and a region-of-interest window which may overlay at least a portion of the first image.

FIG. 4 illustrates a monitor 400 (e.g., 128 in FIG. 1) for presenting an example user interface comprising a first image 402 of an object under examination by an X-ray imaging modality. By way of example, in the context of medical imaging, an X-ray imaging modality may be configured to examine a patient, and a presentation component (not shown) may be configured to provide for presentation on the monitor 400 a first image 402, depicting at least a portion of the patient.

As provided herein, in one embodiment, a region-of-interest representing at least a portion of the object may be identified from the first image 402. For example, in the illustrated embodiment, a region-of-interest window 404 (e.g., represented by dashed lines) provided for presentation by a presentation component (not shown), for example, may be displayed to a user when a user selects an option to focus on a region-of-interest and/or may be presented by default. The region-of-interest window 404 typically defines that region-of-interest, such that the boundaries of the window 404 define boundaries of the region-of-interest, for example.

The region-of-interest window 404 may be configured to overlay at least some of an image, as shown in FIG. 4 with the window 404 overlaying a portion of the first image 402. Moreover, the window 404 may be moved about the image 402 and/or properties of the window 404 may be manipulated (e.g., the window 404 may be increased and/or decreased in size and/or shape to accommodate the varying sizes and/or shapes of objects of interest); the manipulation being either automatic or generated by user interaction/input, for example. By way of example and not limitation, a user may use a mouse to drag one or more boundaries of the window 404 to increase or decrease the size and/or shape of the window 404 and/or the user may select, in an options menu, for example, between predefined sizes for the window 404. Moreover, the user may use a mouse to reposition the window 404 relative to an underlying object. In this way, the window 404 can be maneuvered about the first image 402 and/or resized to identify a region-of-interest in the object as depicted in the first image 402, for example.

It may be appreciated that FIG. 4 and its accompanying description is merely intended to provide an example technique for identifying a region-of-interest. For example, in another embodiment, an automated process may be performed to identify one or more regions-of-interest of an object via a first image as described with respect to the ROI processing component 202 of FIG. 2. For example, object recognition techniques may be utilized to identify desired aspects of the object from the first image based upon shape, density, atomic properties, and/or other properties. In such an example, it may be unnecessary to display a region-of-interest window 404 as provided for in FIG. 4, for example, because the region-of-interest is automatically identified. Although, it one embodiment, a region-of-interest window 404 may be displayed to a user to confirm the automatic identification of a region-of-interest (e.g., the region-of-interest window 404 may overlay the automatically identified region-of-interest, and a user may be given the option to confirm the automatic identification and/or to reject the automatic identification (e.g., and to manually adjust, reposition, resize, etc. the window 404)).

Figure 5:
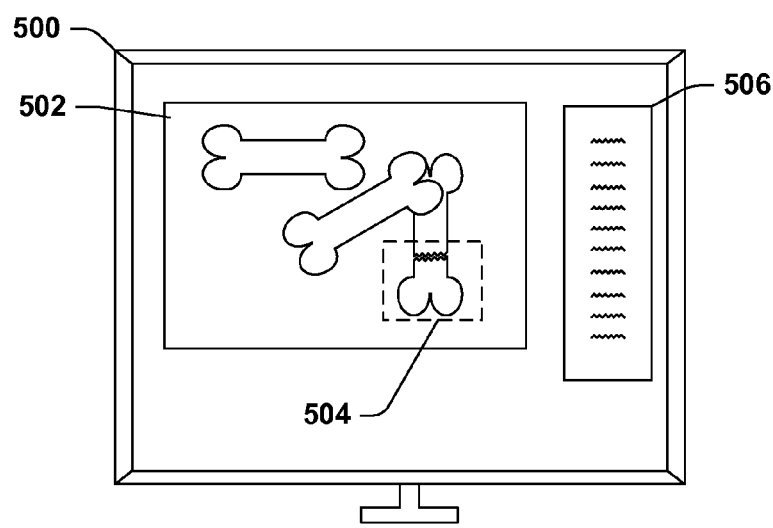
FIG. 5 illustrates an example user interface displaying a menu providing menu options for dynamically adjusting X-ray acquisition parameters.

In one embodiment, a menu displaying options for dynamically adjusting one or more X-ray acquisition parameters may further be presented/displayed, and a user, for example, may select one or more options for adjusting an X-ray acquisition parameter(s) from the menu. By way of example, FIG. 5 illustrates a user interface providing for a menu 506 that may be provided for presentation on a display 500 (e.g., by a presentation component) upon the identification of a region-of interest (e.g., represented within the region-of-interest window 504 (e.g., 404 in FIG. 4)) in a first image 502 (e.g., 402 in FIG. 4). In another embodiment, the menu 506 may be displayed before a region-of-interest is identified and/or maybe triggered based upon some other event besides the identification of a region-of-interest. For example, in one embodiment, a user may select an option from a toolbar which causes the menu 506 to be displayed. In another embodiment, an automatic region-of-interest analysis process may identify suggested adjustments to one or more X-ray acquisition parameters and may highlight these options in the menu 506, for example.

As described with respect to FIG. 2, the menu 506 may provide a way for a user to specify how to adjust one or more X-ray acquisition parameters between a first portion of an examination and a second portion of the examination. By way of example, the menu 506 may provide options for dynamically altering the X-ray tube current, the X-ray tube voltage, the X-ray beam shape (e.g., including variable spatial beam filtering and/or dynamic collimation adjustments, as necessary for 'interior' CT reconstruction, such as 'local' reconstruction, for example), X-ray beam filtration, detector spatial resolution, temporal resolution, digital acquisition filter parameters, image reconstruction filter parameters, and/or region-of-interest spatial resolution, for example, during an examination of an object based upon an identified region-of-interest in a first image produced during a first portion of the examination. In this way, a user may select X-ray acquisition parameters that are to be modified to provide a second image, generated from information acquired during a second portion of the examination (or from a combination of both first and second examination portions), that enhances or changes how an object(s) comprised in the region-of-interest appears (e.g., relative to the appearance of the object(s) in the first image). That is, stated differently, the selection of one or more menu options, along with the identification of a region-of-interest, for example, may be utilized to determine how to adjust one or more X-ray acquisition parameters to create a second image representing the region-of-interest in a different manner relative to the first image, which was generated from a first portion of the examination prior to one or more of the X-ray acquisition parameters being adjusted (e.g., as specified via the selection of one or more options from the menu 506).

It may be appreciated that the presentation of a menu 506 and/or a user's selection of menu options describe merely one example technique for determining how to adjust/set X-ray acquisition parameters. For example, in another embodiment, determining which X-ray acquisition parameters to adjust and/or criteria for adjusting the X-ray acquisition parameters may be automated (e.g., such that the menu 506 is not presented on a display 500). By way of example, in one embodiment, the region-of-interest may be analyzed to determine properties of the region-of-interest (e.g., shape, density, z-effective material number, x-ray total line-integral paths attenuations, etc. of aspects within the region-of-interest). Using such determined properties, computer-implemented software, for example, may determine how the X-ray acquisition parameters should be adjusted. Thus, in one embodiment, a user may have little to no direct and/or interactive input into how the X-ray acquisition parameters are adjusted and/or may merely verify the desireability of the adjustments to the X-ray acquisition parameters as determined by the computer-implemented software, for example.

Figure 6:
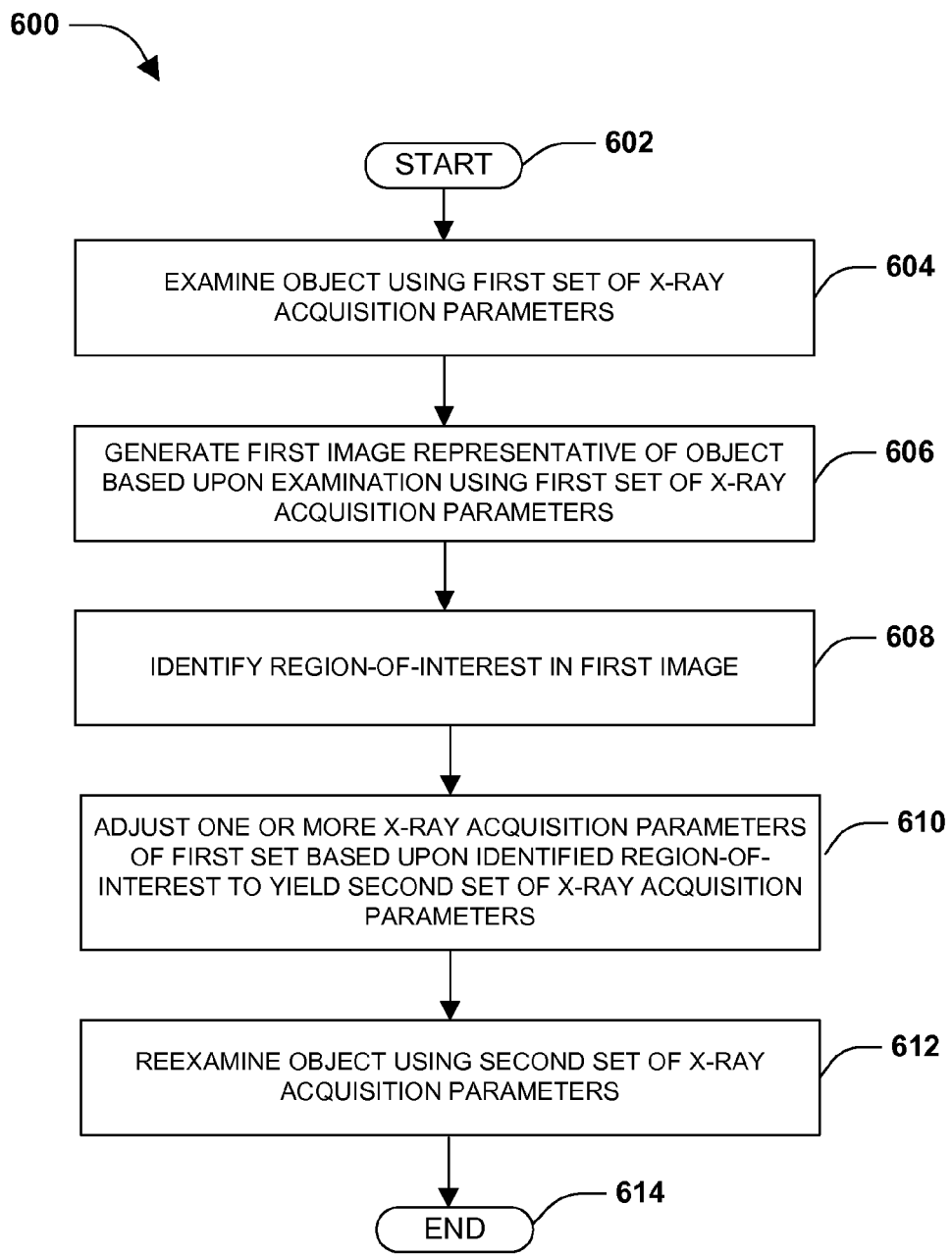
FIG. 6 illustrates an example method for dynamically adjusting X-ray acquisition parameters in an X-ray imaging modality.

FIG. 6 illustrates an example method 600 for dynamically adjusting one or more X-ray acquisition parameters in an X-ray imaging modality. It may be appreciated that the method 600 described herein is merely an example method and is not intended to be interpreted in a limiting manner. Moreover, the arrangement of the acts is merely an example arrangement and other arrangements (e.g., including more or fewer acts) are contemplated to the extent practical.

The example method 600 begins at 602, and an object is examined via the X-ray imaging modality using a first set of X-ray acquisition parameters at 604. For example, the X-ray imaging modality may comprise a computed tomography (CT) system, such as utilized in medical applications to examine a patient, and may be configured to expose the patient to X-ray radiation and to generate an image from the exposure. The first set of X-ray acquisition parameters may be specified by a user of the X-ray imaging modality prior to the examination or may be default parameters selected from a protocol menu specified at a time of manufacturing and possibly further refined prior to the start of the examination by known information about the object and/or based upon a visual examination of the object, for example.

X-ray acquisition parameters refer to parameters that specify how information is acquired and/or what information is acquired during an examination of the object. By way of example and not limitation, x-ray tube current, x-ray tube voltage, x-ray beam shape, longitudinal extent of the examination, detector spatial resolution, temporal resolution, digital acquisition system filter parameters, and/or image reconstruction filter parameters affect how information is acquired and/or what information is acquired. Such parameters may be contrasted with image reconstruction parameters, for example, that specify how data is combined or compiled to generate an image from the examination. In turn, such image reconstruction parameters may be matched or optimized based upon dynamically selected acquisition parameters or visualization task such as a specific diagnostic task or a specific threat detection task, for example.

At 606 in the example method 600, a first image representative of the object is generated based at least in part upon information obtained during the examination using the first set of X-ray acquisition parameters. That is, stated differently, the signals generated during the examination may be converted into image data representative of the object under examination to generate a first image. As previously described, the first image is predominately utilized for identifying a region-of-interest (e.g., as opposed to being utilized for diagnostic purposes). As such, the dose of X-ray radiation administered to the object during the examination using the first set of X-ray acquisition parameters may be different than (e.g., less than) would be required to generate a diagnostic-quality image and may be lower than a dose of radiation applied when the object is reexamined using a second set of X-ray acquisition parameters (e.g., as will be described below at 612), for example.

In one embodiment, given that the first image is predominately utilized for identifying a region-of-interest (e.g., and is not utilized for diagnostic evaluation), the (low) dose of radiation that is applied to the object may cause reconstruction artifacts to be introduced into an image produced from the examination using the first set of X-ray acquisition parameters (e.g., because the dose is not high enough to collect sufficient information from which to generate an image). As such, in one embodiment, generating the first image representative of the object may further comprise co-registering and/or combining historical image data representative of the object with image data yielded from the examination of the object using the first set of X-ray acquisition parameters as further described with respect to FIG. 3. That is, historical image data indicative of the object, which may have been acquired months or years earlier may be co-registered and/or combined with image data from a present-day examination, for example, to produce an image with less reconstruction artifacts than an image that would have been produced merely from the image data yielded from the examination using the first set of X-ray acquisition parameters.

In an embodiment where historical image data is co-registered and/or combined with image data acquired during an examination using a first set of X-ray acquisition parameters, the historical image data may have been acquired with the object in substantially the same orientation as the object is in during the examination using the first set of X-ray acquisition parameters and/or in a different orientation. For example, in a CT imaging modality where volumetric data of the object is acquired, the orientation of the object is substantially immaterial as long the volume represented in the historical image data at least partially corresponds to the volume represented in the image data acquired from the examination using the first set of X-ray acquisition parameters. Moreover, the historical image data is generally not being used to determine a present-day orientation of the object relative to the support article, for example. Rather, the image data acquired from the examination using the first set of X-ray acquisition parameters may be utilized to determine the present-day orientation of the object, for example, and the historical image data may be utilized to supplement the image data acquired from the examination using the first set of X-ray acquisition parameters.

Additionally, a low-dose initial portion of the examination (e.g., a first portion of the examination) may enable co-registration of historical data, such that the beam may be collimated down spatially to cover substantially merely the region-of-interest (ROI) (in the lateral dimensions). The 'limited' or 'local' data sets may then be extended using the historical data, thus substantially reducing (e.g., eliminating) artifacts that are known to be associated with truncated data, for example. In this way, a diagnostic quality examination of the ROI may be enabled at a substantially reduced total dose, for example.

At 608 in the example method 600, a region-of-interest is identified in the first image. As described above with respect to FIGS. 2-5, the region-of-interest may be identified automatically and/or may be identified at least in part via user input. For example, in one embodiment, object recognition techniques may be utilized to identify one or more objects in an image, and a region-of-interest may be defined/identified that comprises an object(s) of interest from the one or more identified objects. For example, a user may specify that a representation of the heart is desirable and the object recognition techniques may be utilized to identify a region of the image that comprises the heart (e.g., which may be identified as the region-of-interest).

In another embodiment, identifying the region-of-interest may comprise displaying and/or providing for a display a region-of-interest window (e.g., such as described with respect to FIG. 4) that defines boundaries of the region-of-interest, for example. Such a region-of-interest window may be configured to overlay at least some of the first image generated at 606 and may be configured to be moved about the first image (e.g., based upon user input). In this way, a user may navigate the first image to identify a region of particular interest within the first image. Moreover, the region-of-interest window may be (re)sizable to provide for increasing and/or decreasing an area and/or volume of the region-of-interest (e.g., which may include providing for a region-of-interest that is substantially equal in size to the image such that the image and the region-of-interest comprise substantially similar boundaries.

At 610 in the example method 600, one or more X-ray acquisition parameters of the first set of X-ray acquisition parameters are adjusted based upon the identified region-of-interest to yield a second set of X-ray acquisition parameters. That is, at least one X-ray acquisition parameter is modified based upon the identified region-of-interest to alter how information/data is acquired and/or processed, for example. This modification may happen concurrently with continued data acquisition and/or may be performed in between data-acquisition sequences for the same object.

As described above with respect to FIGS. 2 and 5, for example, determining how and/or what parameters to adjust may be a function of user input and/or may be automatic based upon the identified region-of-interest and/or the contents of the object represented by the region-of-interest. For example, in one embodiment, a menu displaying menu options for adjusting the one or more X-ray acquisition parameters of the first set may be displayed (e.g., such as upon identifying the region-of-interest). A user, for example, may navigate the menu, selecting one or more X-ray acquisition parameters to adjust, and an indication of the selection(s) from the menu options may be received (e.g., by a menu selection component 204 of FIG. 2). As such, one or more X-ray acquisition parameters may be adjusted according to the received indication to yield the second set of X-ray acquisition parameters.

In another embodiment, at least one X-ray acquisition parameter may be automatically adjusted based at least in part upon the identified region-of-interest. For example, as further described with respect to FIG. 2, in one embodiment, the region-of-interest (e.g., which is manually or automatically identified at 608 in the example method 600) is analyzed to identify features of the region-of-interest and/or the contents represented in the region-of-interest, and it is automatically determined (e.g., by a computer program) how to adjust one or more X-ray acquisition parameters based upon the analysis, or the identified features. For example, the X-ray imaging modality may be configured to adjust an X-ray acquisition parameter to a first value when a heart is identified in the region-of-interest and may be configured to adjust the same X-ray acquisition parameter to a second, different value when a lung is identified in the region-of-interest.

At 612 in the example method 600, the object is reexamined using the second set of X-ray acquisition parameters to generate a second image of the object, or of aspects of the object represented in the region-of-interest. Typically, the second image is intended to be of higher quality than the first image. By way of example, the second image may be of diagnostic-quality whereas the first image may not be of diagnostic quality. As such, the dose of X-ray radiation administered to the object during the examination using the second set of X-ray acquisition parameters may be different (e.g., higher) than the dose of radiation emitted during the examination using the first set of X-ray acquisition parameters (e.g., where the imaging using the first set of X-ray acquisition parameters was performed predominately to determine an orientation of the object relative to the support article and/or to identify a region-of-interest, for example).

The example method 600 ends at 614.

Figure 7:
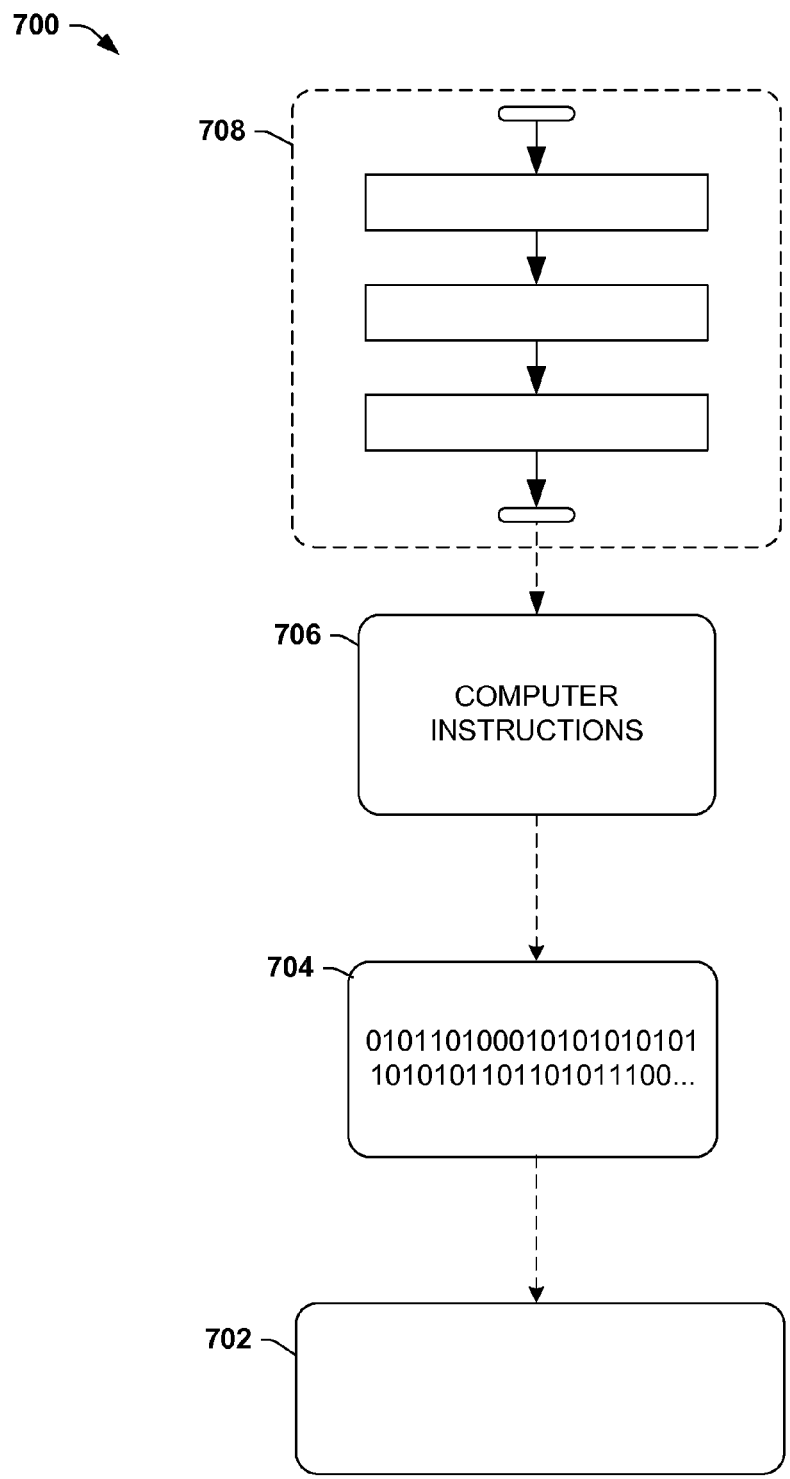
FIG. 7 is an illustration of an example computer-readable medium comprising processor-executable instructions configured to embody one or more of the provisions set forth herein.

Still another embodiment involves a computer-readable medium comprising processor-executable instructions configured to implement one or more of the techniques presented herein. An example computer-readable medium that may be devised in these ways is illustrated in FIG. 7, wherein the implementation 700 comprises a computer-readable medium 702 (e.g., a CD-R, flash drive, DVD-R, or a platter of a hard disk drive), on which is encoded computer-readable data 704. This computer-readable data 704 in turn comprises a set of computer instructions 706 configured to operate according to one or more of the principles set forth herein. In one such embodiment 700, the processor-executable instructions 706 may be configured to perform a method 708, such as at least some of the example method 600 of FIG. 6, for example. In another such embodiment, the processor-executable instructions 606 may be configured to implement a system, such as at least some of the exemplary system 100 of FIG. 1, as at least some of the exemplary system 200 of FIG. 2, and/or as at least some of the exemplary system 300 of FIG. 3, for example. Many such computer-readable media may be devised by those of ordinary skill in the art that are configured to operate in accordance with one or more of the techniques presented herein.

Moreover, the words "example" and/or "exemplary" are used herein to mean serving as an example, instance, or illustration. Any aspect, design, etc. described herein as "example" and/or "exemplary" is not necessarily to be construed as advantageous over other aspects, designs, etc. Rather, use of these terms is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims may generally be construed to mean "one or more" unless specified otherwise or clear from context to be directed to a singular form.

Also, although the disclosure has been shown and described with respect to one or more implementations, equivalent alterations and modifications may occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated example implementations of the disclosure. In addition, while a particular feature of the disclosure may have been disclosed with respect to only one of several implementations, such feature may be combined with one or more other features of the other implementations as may be desired and advantageous for any given or particular application. Furthermore, to the extent that the terms "includes", "having", "has", "with", or variants thereof are used in either the detailed description or the claims, such terms are intended to be inclusive in a manner similar to the term "comprising."

What is claimed is:

1. A method, comprising:
    receiving historical image data representative of an object examined at a first X-ray dosage during a prior examination of the object;
    examining the object at a second X-ray dosage to generate first image data representative of the object at a present orientation, wherein the second X-ray dosage is less than the first X-ray dosage;
    co-registering the historical image data with the first image data to generate second image data representative of the object at the present orientation;
    identifying a region-of-interest of the object in the second image data;
    setting an X-ray acquisition parameter based upon the region-of-interest to yield a set X-ray acquisition parameter; and
    reexamining the object according to the set X-ray acquisition parameter.

2. The method of claim 1, wherein the examining the object at a second X-ray dosage comprises performing a computed tomography (CT) examination on the object.

3. The method of claim 1, comprising:
    analyzing the region-of-interest to identify an anatomical feature of the region-of-interest.

4. The method of claim 1, wherein the setting comprises setting at least one of:
    X-ray tube current,
    X-ray tube voltage,
    X-ray beam shape,
    X-ray beam filtration,
    detector spatial resolution,
    temporal resolution,
    digital acquisition system filter parameters, or
    image generation filter parameters.

5. The method of claim 1, wherein the historical image data is representative of the object at a historical orientation that is different than the present orientation.

6. The method of claim 3, wherein the setting comprises setting the X-ray acquisition parameter based upon the anatomical feature.

7. The method of claim 1, wherein the X-ray acquisition parameter comprises detector spatial resolution.

8. The method of claim 1, comprising displaying a region-of-interest window configured to overlay at least some of the second image data and to be moved about the second image data, wherein the region-of-interest window defines the region-of-interest.

9. The method of claim 8, comprising increasing or decreasing a size of the region-of-interest window based upon user input.

10. The method of claim 1, wherein the setting comprises:
analyzing the region-of-interest to identify a feature of the region-of-interest; and
automatically setting the X-ray acquisition parameter based upon the feature.

11. The method of claim 1, comprising:
presenting a menu displaying menu options for setting the X-ray acquisition parameter; and
receiving an indication of a selection from the menu options,
wherein the setting comprises setting the X-ray acquisition parameter according to the selection.

12. The method of claim 11, wherein the presenting comprises presenting the menu in response to the identifying.

13. A system comprising:
an examination unit configured to examine an object at a first X-ray dosage to generate first image data representative of the object at a present orientation;
a co-registration component configured to:
receive historical image data representative of the object examined at a second X-ray dosage during a prior examination of the object, wherein the first X-ray dosage is less than the second X-ray dosage, and
co-register the historical image data with the first image data to generate second image data representative of the object at the present orientation;
a region-of-interest processing component configured to identify a region-of-interest of the object in the second image data; and
an X-ray parameters component configured to set an X-ray acquisition parameter based upon the region-of-interest to yield a set X-ray acquisition parameter,
wherein the examination unit is configured to reexamine the object according to the set X-ray acquisition parameter.

14. The system of claim 13, wherein the historical image data is representative of the object at a historical orientation that is different than the present orientation.

15. The system of claim 13, wherein the region-of-interest processing component is configured to analyze the region-of-interest to identify an anatomical feature of the region-of-interest, and wherein the X-ray parameters component is configured to set the X-ray acquisition parameter based upon the anatomical feature.

16. The system of claim 13, wherein the X-ray acquisition parameter comprises at least one of a detector spatial resolution or a temporal resolution.

17. The system of claim 13, wherein the examination unit comprises a computed tomography (CT) system.

18. The system of claim 13, comprising a presentation component configured to provide for presentation a region-of-interest window configured to overlay at least some of the second image data and to be moved about the second image data, wherein the region-of-interest window defines the region-of-interest.

19. The system of claim 13, comprising a presentation component configured to provide for presentation of a menu displaying menu options for setting the X-ray acquisition parameter.

20. A computer readable medium comprising computer executable instructions that when executed perform a method, comprising:
receiving historical image data representative of an object examined at a first X-ray dosage during a prior examination of the object;
examining the object at a second X-ray dosage to generate first image data representative of the object at a present orientation, wherein the second X-ray dosage is less than the first X-ray dosage;
co-registering the historical image data with the first image data to generate second image data representative of the object at the present orientation;
identifying a region-of-interest of the object in the second image data;
setting an X-ray acquisition parameter based upon the region-of-interest to yield a set X-ray acquisition parameter; and
reexamining the object according to the set X-ray acquisition parameter.

* * * * *